US010610316B2

(12) United States Patent
Swarup et al.

(10) Patent No.: US 10,610,316 B2
(45) Date of Patent: *Apr. 7, 2020

(54) SYSTEM AND METHOD FOR ALIGNING WITH A REFERENCE TARGET

(71) Applicant: INTUITIVE SURGICAL OPERATIONS, INC., Sunnyvale, CA (US)

(72) Inventors: Nitish Swarup, Sunnyvale, CA (US); Paul G. Griffiths, Santa Clara, CA (US); Brandon D. Itkowitz, San Jose, CA (US); Michael Hanuschik, Mountain View, CA (US); Thomas R. Nixon, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/052,555

(22) Filed: Aug. 1, 2018

(65) Prior Publication Data

US 2018/0338808 A1  Nov. 29, 2018

Related U.S. Application Data

(63) Continuation of application No. 15/126,983, filed as application No. PCT/US2015/021097 on Mar. 17, 2015, now Pat. No. 10,064,689.

(Continued)

(51) Int. Cl.
*A61B 34/00* (2016.01)
*A61B 1/00* (2006.01)
(Continued)

(52) U.S. Cl.
CPC .......... *A61B 34/70* (2016.02); *A61B 1/00149* (2013.01); *A61B 34/30* (2016.02);
(Continued)

(58) Field of Classification Search
CPC ..... A61B 34/70; A61B 1/00149; A61B 34/30; A61B 2034/305; A61B 2034/304;
(Continued)

(56) References Cited

U.S. PATENT DOCUMENTS

| 5,465,037 A | 11/1995 | Huissoon et al. |
| 7,763,015 B2 | 7/2010 | Cooper et al. |

(Continued)

FOREIGN PATENT DOCUMENTS

| EP | 0571827 A1 | 12/1993 |
| EP | 1234641 A1 | 8/2002 |

(Continued)

OTHER PUBLICATIONS

Extended European Search Report for Application No. 15765922.8, dated Oct. 18, 2017, 8 pages.

(Continued)

*Primary Examiner* — Jaime Figueroa
(74) *Attorney, Agent, or Firm* — Artegis Law Group, LLP

(57) ABSTRACT

A system and method of aligning with a reference target includes a computer-assisted device. The computer-assisted device includes a link, one or more first joints coupled proximally to the link, an articulated arm comprising one or more second joints coupled distally to the link, the articulated arm configured to couple to an instrument, and a control unit. The control unit is configured to position or orient the link, using the one or more first joints, based on at least one reference of the instrument selected from the group consisting of a reference point associated with the instrument and a reference orientation of the instrument. The control unit is further configured to maintain, while positioning or orienting the link and by using the one or more (Continued)

second joints, a position or an orientation of the instrument relative to a workspace in accordance with the at least one reference of the instrument.

21 Claims, 5 Drawing Sheets

Related U.S. Application Data

(60) Provisional application No. 62/024,887, filed on Jul. 15, 2014, provisional application No. 61/954,261, filed on Mar. 17, 2014.

(51) Int. Cl.
  *B25J 9/16* (2006.01)
  *A61B 34/30* (2016.01)
  *A61B 17/00* (2006.01)
  *A61B 34/20* (2016.01)

(52) U.S. Cl.
  CPC .......... *B25J 9/1607* (2013.01); *B25J 9/1633* (2013.01); *A61B 2017/00017* (2013.01); *A61B 2034/2059* (2016.02); *A61B 2034/301* (2016.02); *A61B 2034/304* (2016.02); *A61B 2034/305* (2016.02)

(58) Field of Classification Search
  CPC ...... A61B 2034/301; A61B 2034/2059; A61B 2017/00017; B25J 9/1633; B25J 9/1607
  USPC .................................................. 700/245, 251
  See application file for complete search history.

(56) References Cited

U.S. PATENT DOCUMENTS

| | | | |
|---|---|---|---|
| 7,819,859 B2 | 10/2010 | Prisco et al. |
| 7,837,674 B2 | 11/2010 | Cooper |
| 8,004,229 B2 | 8/2011 | Nowlin et al. |
| 8,271,130 B2 | 9/2012 | Hourtash |
| 8,400,094 B2 | 3/2013 | Schena |
| 8,541,970 B2 | 9/2013 | Nowlin et al. |
| 8,620,473 B2 | 12/2013 | Diolaiti et al. |
| 8,624,537 B2 | 1/2014 | Nowlin et al. |
| 8,749,189 B2 | 6/2014 | Nowlin et al. |
| 8,749,190 B2 | 6/2014 | Nowlin et al. |
| 8,786,241 B2 | 7/2014 | Nowlin et al. |
| 8,816,628 B2 | 8/2014 | Nowlin et al. |
| 8,823,308 B2 | 9/2014 | Nowlin et al. |
| 8,918,211 B2 | 12/2014 | Diolaiti et al. |
| 9,078,686 B2 | 7/2015 | Schena |
| 9,084,623 B2 | 7/2015 | Gomez et al. |
| 9,107,683 B2 | 8/2015 | Hourtash et al. |
| 9,138,129 B2 | 9/2015 | Diolaiti |
| 9,296,104 B2 | 3/2016 | Swarup et al. |
| 9,333,042 B2 | 5/2016 | Diolaiti et al. |
| 9,345,544 B2 | 5/2016 | Hourtash et al. |
| 9,375,284 B2 | 6/2016 | Hourtash |
| 9,415,510 B2 | 8/2016 | Hourtash et al. |
| 9,468,501 B2 | 10/2016 | Hourtash et al. |
| 9,469,034 B2 | 10/2016 | Diolaiti et al. |
| 9,492,235 B2 | 11/2016 | Hourtash et al. |
| 9,492,927 B2 | 11/2016 | Diolaiti et al. |
| 9,526,581 B2 | 12/2016 | Bodduluri et al. |
| 9,710,921 B2 | 7/2017 | Wong et al. |
| 1,006,468 A1 | 9/2018 | Swarup et al. |
| 1,007,093 A1 | 9/2018 | Itkowitz et al. |
| 2003/0021107 A1 | 1/2003 | Howell et al. |
| 2003/0025473 A1 | 2/2003 | Nagata et al. |
| 2006/0025668 A1 | 2/2006 | Peterson et al. |
| 2009/0048611 A1 | 2/2009 | Funda et al. |
| 2010/0138183 A1 | 6/2010 | Jensen et al. |
| 2010/0204713 A1 | 8/2010 | Ruiz |
| 2010/0274087 A1* | 10/2010 | Diolaiti ............ A61B 90/37 600/118 |
| 2011/0054303 A1 | 3/2011 | Barrick et al. |
| 2011/0238082 A1 | 9/2011 | Wenderow et al. |
| 2013/0085510 A1 | 4/2013 | Stefanchik et al. |
| 2013/0096576 A1 | 4/2013 | Cooper et al. |
| 2014/0031983 A1 | 1/2014 | Low et al. |
| 2014/0039681 A1 | 2/2014 | Bowling et al. |
| 2014/0052153 A1 | 2/2014 | Griffiths et al. |
| 2014/0052154 A1 | 2/2014 | Griffiths et al. |
| 2014/0236175 A1* | 8/2014 | Cooper ............... A61B 34/30 606/130 |
| 2014/0305995 A1* | 10/2014 | Shelton, IV ..... A61B 17/07207 227/180.1 |
| 2014/0316430 A1 | 10/2014 | Hourtash et al. |
| 2014/0358161 A1 | 12/2014 | Hourtash et al. |
| 2015/0032126 A1 | 1/2015 | Nowlin et al. |
| 2015/0051733 A1 | 2/2015 | Nowlin et al. |
| 2015/0150639 A1 | 6/2015 | Diolaiti et al. |
| 2016/0030124 A1 | 2/2016 | Kishi et al. |
| 2017/0181806 A1 | 6/2017 | Itkowitz et al. |
| 2018/0344417 A1 | 12/2018 | Itkowitz et al. |
| 2019/0117313 A1 | 4/2019 | Crawford |

FOREIGN PATENT DOCUMENTS

| | | | |
|---|---|---|---|
| EP | 1642690 A2 | 4/2006 |
| JP | H0699372 A | 4/1994 |
| JP | 2011206312 A | 10/2011 |
| WO | WO-2006079108 A1 | 7/2006 |
| WO | WO-2006124390 A2 | 11/2006 |
| WO | WO-2011143023 A1 | 11/2011 |
| WO | WO-2011143024 A1 | 11/2011 |
| WO | WO-2012158458 A2 | 11/2012 |
| WO | WO-2013048957 A1 | 4/2013 |
| WO | WO-2013181503 A1 | 12/2013 |
| WO | WO-2013181507 A1 | 12/2013 |
| WO | WO-2013181516 A1 | 12/2013 |
| WO | WO-2014028702 A1 | 2/2014 |
| WO | WO-2014028703 A1 | 2/2014 |
| WO | WO-2014146095 A1 | 9/2014 |
| WO | WO-2014146107 A1 | 9/2014 |
| WO | WO-2014146113 A1 | 9/2014 |
| WO | WO-2014146119 A1 | 9/2014 |
| WO | WO-2014146120 A1 | 9/2014 |
| WO | WO-2015142798 A1 | 9/2015 |
| WO | WO-2015142947 A1 | 9/2015 |

OTHER PUBLICATIONS

International Search Report and Written Opinion for Application No. PCT/US15/21089, dated Jun. 19, 2015, 10 pages.
International Search Report and Written Opinion for Application No. PCT/US15/21097, dated Jul. 1, 2015, 16 pages.
Extended European Search Report for Application No. EP15765353.6, dated Nov. 13, 2017, 9 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

SYSTEM AND METHOD FOR ALIGNING WITH A REFERENCE TARGET

RELATED APPLICATIONS

The present application is a continuation of U.S. patent application Ser. No. 15/126,983 filed Sep. 16, 2016, which is the U.S. national phase of International Application No. PCT/US2015/021097 filed Mar. 17, 2015, which designated the U.S. and claims priority to U.S. Provisional Patent Application No. 61/954,261 entitled "System and Method for Aligning with a Reference Target" filed Mar. 17, 2014 and U.S. Provisional Patent Application No. 62/024,887 entitled "System and Method for Aligning with a Reference Target" filed Jul. 15, 2014, the entire contents of each of which are herein incorporated by reference.

TECHNICAL FIELD

The present disclosure relates generally to operation of devices with articulated arms and more particularly to aligning with a reference target.

BACKGROUND

More and more devices are being replaced with autonomous and semiautonomous electronic devices. This is especially true in the hospitals of today with large arrays of autonomous and semiautonomous electronic devices being found in operating rooms, interventional suites, intensive care wards, emergency rooms, and the like. For example, glass and mercury thermometers are being replaced with electronic thermometers, intravenous drip lines now include electronic monitors and flow regulators, and traditional hand-held surgical instruments are being replaced by computer-assisted medical devices.

These electronic devices provide both advantages and challenges to the personnel operating them. Many of these electronic devices may be capable of autonomous or semi-autonomous motion of one or more articulated arms and/or end effectors. Before these articulated arms and their end effectors may be used, they are typically moved to or near a desired working position and orientation. This movement may be performed by teleoperation or remote operation using one or more user input controls. As the complexity of these electronic devices increases and the articulated arms include large numbers of degrees of freedom, movement into the desired working position and orientation by teleoperation may become complex and/or time consuming. In addition, operators of these electronic devices may not always be aware of the limits of motion of one or more of the articulated arms or the end effectors, such as medical instruments, coupled to those articulated arms. As a consequence, the operators may not always provide the best initial working position of the articulated arms that provides for the best range of motion after set-up.

Accordingly, improved methods and systems for the initial positioning of articulated arms and their end effectors are desirable.

SUMMARY

Consistent with some embodiments, a computer-assisted medical device includes an orientation platform, one or more first joints proximal to the orientation platform, one or more second joints distal to the orientation platform, one or more links distal to the orientation platform, a reference instrument coupled to orientation platform by the second joints and the links; and a control unit coupled to the first joints and the second joints. The control unit determines a pose of the reference instrument. The pose includes a reference point and a reference orientation. The control unit further positions the orientation platform over the reference point using the first joints, rotates the orientation platform to align the orientation platform with the reference orientation using the first joints, and maintains the pose of the reference instrument using the second joints.

Consistent with some embodiments, a method of controlling motion in a medical device includes determining a pose of a reference instrument of the medical device. The pose includes a reference point and a reference orientation. The method further includes positioning an orientation platform of the medical device over the reference point using one or more first joints, rotating the orientation platform to align the orientation platform with the reference orientation using the first joints, and maintaining the pose of the reference instrument using one or more second joints. The one or more first joints are proximal to the orientation platform. The one or more second joints are distal to the orientation platform and proximal to the reference instrument.

Consistent with some embodiments, a non-transitory machine-readable medium comprising a plurality of machine-readable instructions which when executed by one or more processors associated with a medical device are adapted to cause the one or more processors to perform a method. The method includes determining a pose of a reference instrument of the medical device. The pose includes a reference point and a reference orientation. The method further includes positioning an orientation platform of the medical device over the reference point using one or more first joints, rotating the orientation platform to align the orientation platform with the reference orientation using the first joints, and maintaining the pose of the reference instrument using one or more second joints. The one or more first joints are proximal to the orientation platform. The one or more second joints are distal to the orientation platform and proximal to the reference instrument.

In the figures, elements having the same designations have the same or similar functions.

DETAILED DESCRIPTION

In the following description, specific details are set forth describing some embodiments consistent with the present disclosure. It will be apparent to one skilled in the art, however, that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Figure 1:
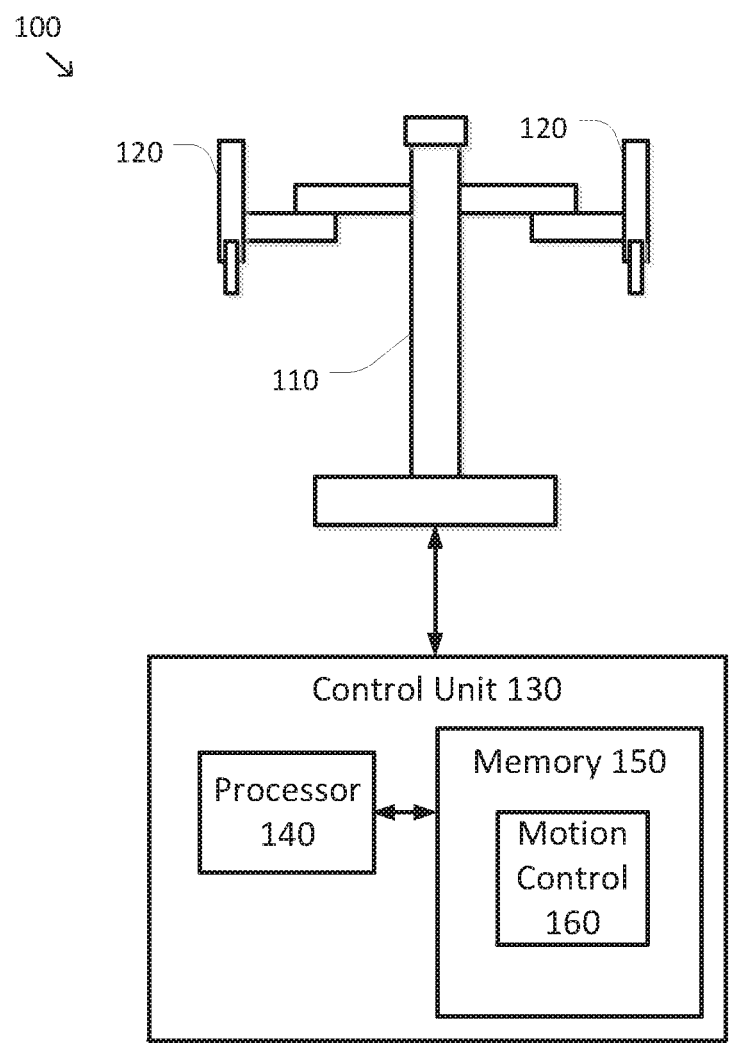
FIG. 1 is a simplified diagram of a computer-assisted system according to some embodiments.

FIG. 1 is a simplified diagram of a computer-assisted system 100 according to some embodiments. As shown in FIG. 1, computer-assisted system 100 includes a device 110 with one or more movable or articulated arms 120. Each of the one or more articulated arms 120 may support one or more end effectors. In some examples, device 110 may be consistent with a computer-assisted surgical device. The one or more articulated arms 120 each provide support for surgical instruments, imaging devices, and/or the like. Device 110 may further be coupled to an operator workstation (not shown), which may include one or more master controls for operating the device 110, the one or more articulated arms 120, and/or the end effectors. In some embodiments, device 110 and the operator workstation may correspond to a da Vinci® Surgical System commercialized by Intuitive Surgical, Inc. of Sunnyvale, Calif. In some embodiments, computer-assisted surgical devices with other configurations, fewer or more articulated arms, and/or the like may be used with computer-assisted system 100.

Device 110 is coupled to a control unit 130 via an interface. The interface may include one or more cables, connectors, and/or buses and may further include one or more networks with one or more network switching and/or routing devices. Control unit 130 includes a processor 140 coupled to memory 150. Operation of control unit 130 is controlled by processor 140. And although control unit 130 is shown with only one processor 140, it is understood that processor 140 may be representative of one or more central processing units, multi-core processors, microprocessors, microcontrollers, digital signal processors, field programmable gate arrays (FPGAs), application specific integrated circuits (ASICs), and/or the like in control unit 130. Control unit 130 may be implemented as a stand-alone subsystem and/or board added to a computing device or as a virtual machine. In some embodiments, control unit may be included as part of the operator workstation and/or operated separately from, but in coordination with the operator workstation.

Memory 150 may be used to store software executed by control unit 130 and/or one or more data structures used during operation of control unit 130. Memory 150 may include one or more types of machine readable media. Some common forms of machine readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

As shown, memory 150 includes a motion control application 160 that may be used to support autonomous and/or semiautonomous control of device 110. Motion control application 160 may include one or more application programming interfaces (APIs) for receiving position, motion, and/or other sensor information from device 110, exchanging position, motion, and/or collision avoidance information with other control units regarding other devices, and/or planning and/or assisting in the planning of motion for device 110, articulated arms 120, and/or the end effectors of device 110. And although motion control application 160 is depicted as a software application, motion control application 160 may be implemented using hardware, software, and/or a combination of hardware and software.

In some embodiments, computer-assisted system 100 may be found in an operating room and/or an interventional suite. And although computer-assisted system 100 includes only one device 110 with two articulated arms 120, one of ordinary skill would understand that computer-assisted system 100 may include any number of devices with articulated arms and/or end effectors of similar and/or different design from device 110. In some examples, each of the devices may include fewer or more articulated arms and/or end effectors.

Figure 2:
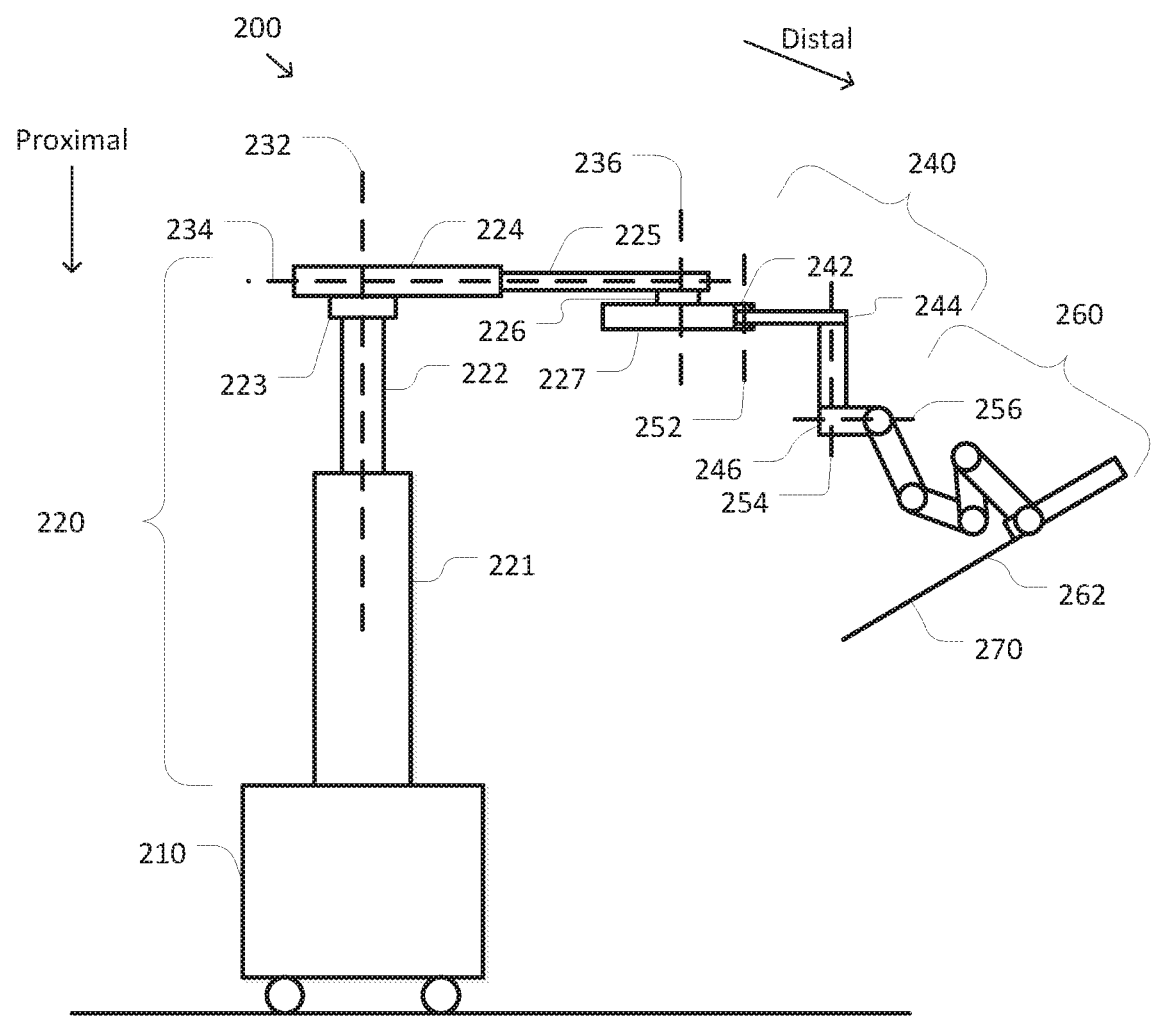
FIG. 2 is a simplified diagram showing a computer-assisted device according to some embodiments.

FIG. 2 is a simplified diagram showing a computer-assisted device 200 according to some embodiments. For example, the computer-assisted device 200 may be consistent with computer-assisted device 110. As shown in FIG. 2, the computer-assisted device 200 includes various links and joints. The computer-assisted device generally has three different sets of links and joints. Starting at the proximal end with a mobile cart 210 is a set-up structure 220. Coupled to a distal end of the set-up structure is a series of set-up joints 240. And coupled to a distal end of the set-up joints 240 is a manipulator 260, such as a universal surgical manipulator. In some examples, the series of set-up joints 240 and manipulator 260 may correspond to one of the articulated arms 120. And although computer-assisted device 200 is shown with only one series of set-up joints 240 and a corresponding manipulator 260, one of ordinary skill would understand that the computer-assisted device 200 may include more than one series of set-up joints 240 and corresponding manipulators 260 so that the computer-assisted device 200 is equipped with multiple articulated arms.

As shown, the computer-assisted device 200 is mounted on the mobile cart 210. The mobile cart 210 enables the computer-assisted device 200 to be transported from location to location, such as between operating rooms or within an operating room to better position the computer-assisted device 200 near a patient table. The set-up structure 220 is mounted on the mobile cart 210. As shown in FIG. 2, the set-up structure 220 includes a two part column including column links 221 and 222. Coupled to the upper or distal end of the column link 222 is a shoulder joint 223. Coupled to the shoulder joint 223 is a two-part boom including boom links 224 and 225. At the distal end of the boom link 225 is a wrist joint 226, and coupled to the wrist joint 226 is an orientation platform 227.

The links and joints of the set-up structure 220 include various degrees of freedom for changing the position and orientation (i.e., the pose) of the orientation platform 227. For example, the two-part column may be used to adjust a height of the orientation platform 227 by moving the shoulder joint 223 up and down along an axis 232. The orientation platform 227 may additionally be rotated about the mobile cart 210, the two-part column, and the axis 232 using the shoulder joint 223. The horizontal position of the orientation platform 227 may also be adjusted along an axis 234 using the two-part boom. And the orientation of the orientation platform 227 may also adjusted by rotation about an axis 236 using the wrist joint 226. Thus, subject to the motion limits of the links and joints in the set-up structure 220, the position of the orientation platform 227 may be adjusted vertically above the mobile cart 210 using the two-part column. The positions of the orientation platform 227 may also be adjusted radially and angularly about the mobile cart 210 using the two-part boom and the shoulder joint 223, respectively. And the angular orientation of the orientation platform 227 may also be changed using the wrist joint 226.

The orientation platform 210 may be used as a mounting point for one or more articulated arms. The ability to adjust the height, horizontal position, and orientation of the orientation platform 227 about the mobile cart 210 provides a flexible set-up structure for positioning and orienting the one or more articulated arms about a work space, such as a patient, located near the mobile cart 210. FIG. 2 shows a single articulated arm coupled to the orientation platform using a first set-up joint 242. And although only one articulated arm is shown, one of ordinary skill would understand that multiple articulated arms may be coupled to the orientation platform 227 using additional first set-up joints. An example of this is described in further detail with respect to FIGS. 3A and 3B.

The first set-up joint 242 forms the most proximal portion of the set-up joints 240 section of the articulated arm. The set-up joints 240 may further include a series of joints and links. As shown in FIG. 2, the set-up joints 240 include at least links 244 and 246 coupled via one or more joints (not expressly shown). The joints and links of the set-up joints 240 include the ability to rotate the set-up joints 240 relative to the orientation platform 227 about an axis 252 using the first set-up joint 242, adjust a height of the link 246 relative to the orientation platform along an axis 254, and rotate the manipulator at least about an axis 256 at the distal end of the link 246. The set-up joints 240 may further include additional joints, links, and axes permitting additional degrees of freedom for altering a pose of the manipulator 260 relative to the orientation platform 227.

The manipulator 260 is coupled to the distal end of the set-up joints 240 and includes additional links and joints that permit control over a pose of an end effector or instrument 262 mounted at a distal end of the manipulator 260. The degrees of freedom in the manipulator 260 may permit at least control of the roll, pitch, and yaw of the instrument 262 relative to the distal end of the set-up joints 240. In some examples, the degrees of freedom in the manipulator 260 may further include the ability to advance and/or retreat the instrument 262 about a longitudinal axis of the instrument 262. In some examples, the degrees of freedom of the set-up joints 240 and the manipulator 260 may further be controlled so as to maintain a remote center 270 about a point on the instrument 262. In some examples, the remote center 270 may correspond to a surgical port in a patient so that as the instrument 262 is used, the remote center 270 remains stationary to limit stresses on the anatomy of the patient at the remote center 270. In some examples, the manipulator 260 may be consistent with a universal surgical manipulator for use with the da Vinci® Surgical System commercialized by Intuitive Surgical, Inc. of Sunnyvale, Calif. In some examples, the instrument 262 may be an imaging device such as an endoscope, a gripper, a surgical tool such as a cautery or a scalpel, and/or the like.

Given the large number of degrees of freedom in the set-up structure 220, the set-up joints 240, and the manipulator 260, it is not always an easy task to determine the best positions of each of the joints so that a pose of the manipulator 260 and, more importantly, a pose of the instrument 262 are maintained as desired. Further, as the desired poses of the manipulator 260 and the instrument 262 are adjusted during operation of the computer-assisted device, suitable flexibility in ranges of motion and orientation should be available so that the desired poses may be obtained without reaching a range of motion limit on any of the joints in the set-up joints 240 or the manipulator 260. To accomplish this, poses of the set-up structure 220 and the orientation platform are typically selected during a set-up phase or targeting operation so that the joints in the set-up joints 240 and the manipulator 260 are located near a center of their respective ranges of motion while at the same time establishing or maintaining a desired pose of the instrument 262 and/or a position of the remote center 270. For the computer-assisted device 200 of FIG. 2, this may generally correspond to poses for the orientation platform 227, the set-up joints 240, and the manipulator 260 so that an approximate rotational center point of the orientation platform 227 (e.g., the axis 236 about which the wrist joint 226 rotates) is located vertically over the remote center 270 and the orientation platform 227 is rotated so that the first set-up joint 242 is approximately near its center of motion. In some examples, the height of the orientation platform 227 may further be adjusted relative to the remote center 270 to a suitable working height.

Figure 3A:
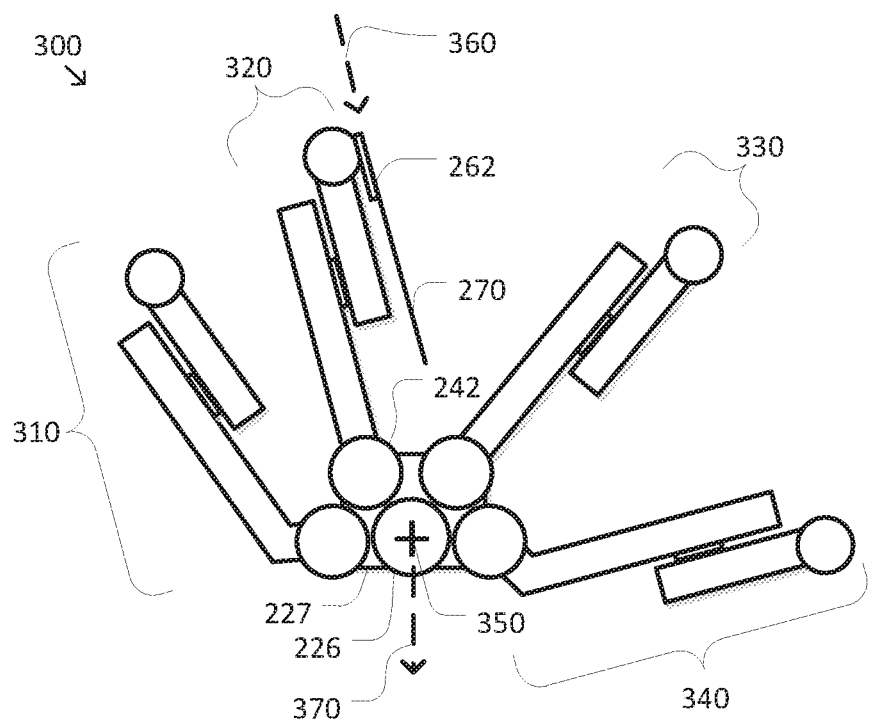
FIGS. 3A and 3B are simplified diagrams showing a top view of poses of the orientation platform of FIG. 2 before and after a targeting operation according to some embodiments.
Figure 3B:
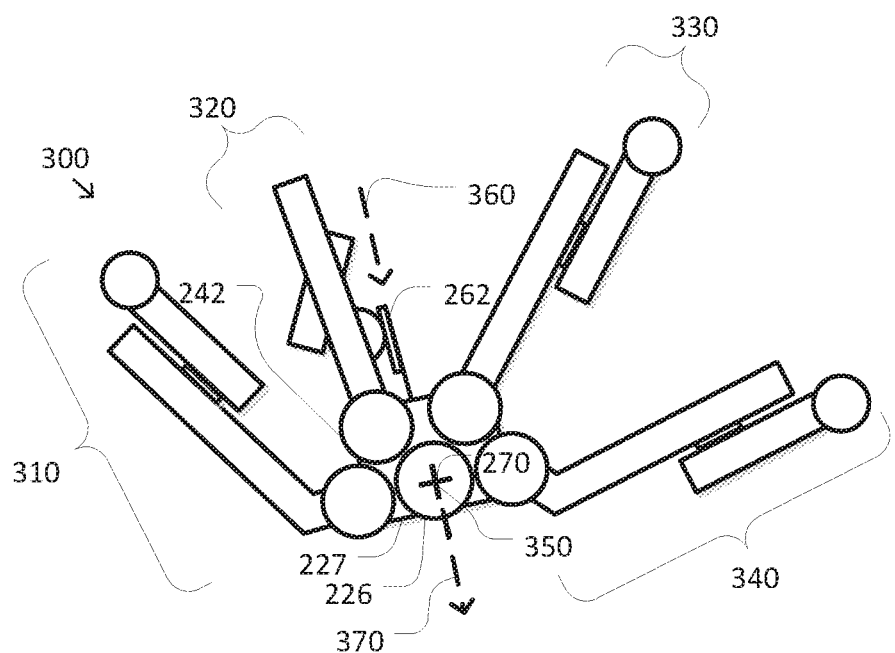

FIGS. 3A and 3B are simplified diagrams showing a top view of poses of the orientation platform 227 of FIG. 2 before and after a targeting operation according to some embodiments. FIG. 3A shows a pose of a portion 300 of a computer-assisted device, such as computer assisted device 200, before the targeting operation. The portion 300 of the computer-assisted device shown in FIG. 3A corresponds to those portions of the computer-assisted device beginning at the orientation platform 227 and links and joints distal to the orientation platform 227. As shown in FIG. 3A, four articulated arms 310-340 are coupled to the orientation platform 227, although one of ordinary skill would understand that any other number of articulated arms may be used. Each of the four articulated arms 310-340 may include different set-up joints, manipulators, and/or instruments. As shown, the four articulated arms include two interior arms 320 and 330, which are located between two exterior arms 310 and 340. An instrument on one of the articulated arms 310-340, typically one of the interior arms 320 or 330, is chosen as a reference target for the targeting operation. For simplicity of explanation, the instrument 262 on articulated arm 320 is being selected as the reference target, although any of the instruments on the other articulated arms may also be selected as the reference target.

Before the targeting operation begins, the instrument 262 and the remote center 270 are typically positioned and oriented within the work space to help specify a region of interest in the work space. In some examples, the instrument 262 and the remote center 270 may be positioned and/or oriented relative to a patient's anatomy. In some examples, the instrument 262 may be inserted through a surgical port on the patient with the remote center 270 being positioned at the surgical port. In some examples, a surgeon and/or other medical personnel may manually position and orient the instrument 262 and the remote center 270 using a clutching feature of the articulated arm 320. In some examples, the instrument 262 may correspond to an endoscope, and the endoscope may be positioned and/or oriented toward a target portion of the patient's anatomy. Once the instrument 262 is positioned and oriented, it is important to maintain that position and orientation during the targeting operation to reduce the likelihood of any injury to the patient and/or damage to the instrument 262. In some examples, for the purposes of the targeting operation, the remote center 270 may correspond to the position of the instrument 262 and an orientation axis 360 may correspond to the orientation of the instrument 262 with the orientation axis 360 being aligned with a shaft of the instrument 262. In some examples, once the instrument 262 is positioned and oriented, the surgeon and/or the other medical personnel may start the targeting operation using a control located on articulated arm 320 and/or at an operator console.

In some embodiments, one of the goals of the targeting operation may be to align a rotational center 350 of the orientation platform 227, such as the rotational center of the wrist joint 226, so that it is vertically above the remote center 270. Another goal of the targeting operation may be to rotate the orientation platform 227 so that a front face of the orientation platform is in alignment with the horizontal component of the orientation axis 360. In some examples, when the orientation axis 360 is vertical, this orientation goal may be omitted. In some examples, the orientation of the front face may correspond to a front face orientation vector 370. In some examples, this rotation may orient the articulated arms 310-340 near centers of the ranges of motion of their respective first set-up joints. In some examples, an additional goal of the targeting operation may be to adjust a height of the orientation platform 227 relative to the remote center 270 to place vertical adjustment joints in the articulated arm 320 near a center of their respective range of movement, to provide a suitable working distance between the orientation platform 227 and the remote center 270 to allow for adequate space for manipulating articulated arm 320 without collision with the orientation platform 227, to provide suitable separation between the orientation platform 227 and the remote center 270 to maintain a sterile field around the remote center 270, and/or to maintain a predetermined distance between the orientation platform 227 and the remote center 270 as determined by an operator.

FIG. 3B shows changes in the position and orientation of the portion 300 of the computer-assisted device as a result of the targeting operation. As shown, the rotational center 350 of the orientation platform 227 is moved so that it aligns vertically with the remote center 270. Further, the orientation platform 227 is rotated so that the front face orientation vector 370 is aligned with the horizontal component of the orientation axis 360. FIG. 3B further shows that the positions of the various joints in the set-up joints and the manipulator of articulated arm 320 are altered to compensate for the changes in the relative position and orientation of the instrument 262 with respect to the orientation platform 227.

To achieve these goals, the position of the remote center 270 and the orientation of the orientation axis 360 are determined using sensors for monitoring the positions of the joints in the computer-assisted device and one or more kinematic models of the computer assisted device. Joints in the set-up structure proximal to the orientation platform 227 are adjusted to move the rotational center 350 over the remote center 270 and the orientation platform 227 is rotated to align the front face orientation vector 370 with the horizontal component of the orientation axis 360. In some examples, joints in the set-up structure may be adjusted to change the height of the orientation platform 227. In some examples, when the set-up structure corresponds to the set-up structure 220 of FIG. 2, the rotational center 350 may also be aligned by changing the length of the two-part boom and rotating the shoulder joint 223, the orientation platform 227 may be rotated using the wrist joint 226, and the height of the orientation platform 227 may be adjusted using the two-part column. While the set-up structure is being moved, the joints in the set-up joints and the manipulator of the articulated arm 320 are adjusted to compensate for the movement and reorientation of the orientation platform 227. This is done to maintain a fixed position of the remote center 270 and a fixed orientation of the orientation axis 360 even though the relative position and orientation of the instrument 262 relative to the orientation platform 227 are changing. In some examples, the joint sensors and one or more kinematic models, and/or inverse Jacobian transposes may be used to determine the joint changes in the set-up joints and the manipulator. In some examples, the position of the remote center 270 and the orientation of the orientation axis 360 may further be maintained using resistance from the patient port and/or by the surgeon and/or other medical personnel. In addition, the other articulated arms 310, 330, and/or 340 may move along with the orientation platform 227. In some embodiments, collision avoidance algorithms may also be used to prevent collisions between the articulated arms 310-340 and between the articulated arms 310-340 and the set-up structure proximal to the orientation platform 227.

In some embodiments, one or more of the joints of the articulated arms 310-340 may be placed in a float state while the orientation platform 227 is in motion. Free and/or mostly free movement of each of the joints in the float state is permitted. In some examples, the joints being placed in the float state may be a subset of the joints in the respective articulated arm 310-340. In some examples, this permits these joints to react to reduce and/or mitigate the effects of external stimulus applied to the respective articulated arm 310-340. In some examples, brakes on each of the joints in the float state, which are non-actuated joints, may be released allowing motion of each of the non-actuated joints. In some examples, each of the joints in the float state, which are actuated joints, may be commanded to move to the actual positions and/or actual velocities determined for those respective joints based on values from one or more sensors associated with the articulated joints and/or the articulated arms 310-340 and/or one or more kinematic models. In some examples, setting the command positions of a feedback controller of the actuated joints to the actual positions and/or the command velocities of the feedback controller to the actual joint velocities gives the impression that the actuated joints are moving freely, and when gravity compensation is also being applied, then also with the impression of apparent weightlessness.

In some embodiments, the movement of the joints in the float state may be subject to damping. To reduce and/or prevent unrestricted and/or wild movement of the articulated arm while in the float state, one or more of the joints placed in the float state may be subject to some form of damped motion. For example, it may not be desirable for any of the articulated arms 310-340 that is subject to a strong external stimulus, such as a hard collision, to move away from the strong external stimulus without some limitation. Constraining the float state movement of the articulated arms 310-340 may reduce the risks of injury and/or damage caused by a fast moving articulated arm. In some examples, the damped motion may be implemented on non-actuated joints by partially releasing the brakes so as to place a drag on movement of the non-actuated joints. In some examples, the brakes may be partially released by controlling one or more voltages, currents, duty cycles, and/or the like of signals used to control the brakes. In some examples, the damped motion may be implemented on actuated joints by commanding the actuated joints to move a portion of the distance behind the actual position based on direction of motion, by increasing a derivative constant in the feedback controller without significantly affecting its stability margins, and/or by introducing a backward current and/or voltage on the actuators of the actuated joints to emulate a resisting force and/or torque. In some examples, the damped motion may be implemented on actuated joints by commanding the velocities of the actuated joints to a value below the joint velocities determined based on the corresponding sensor values.

Figure 4:
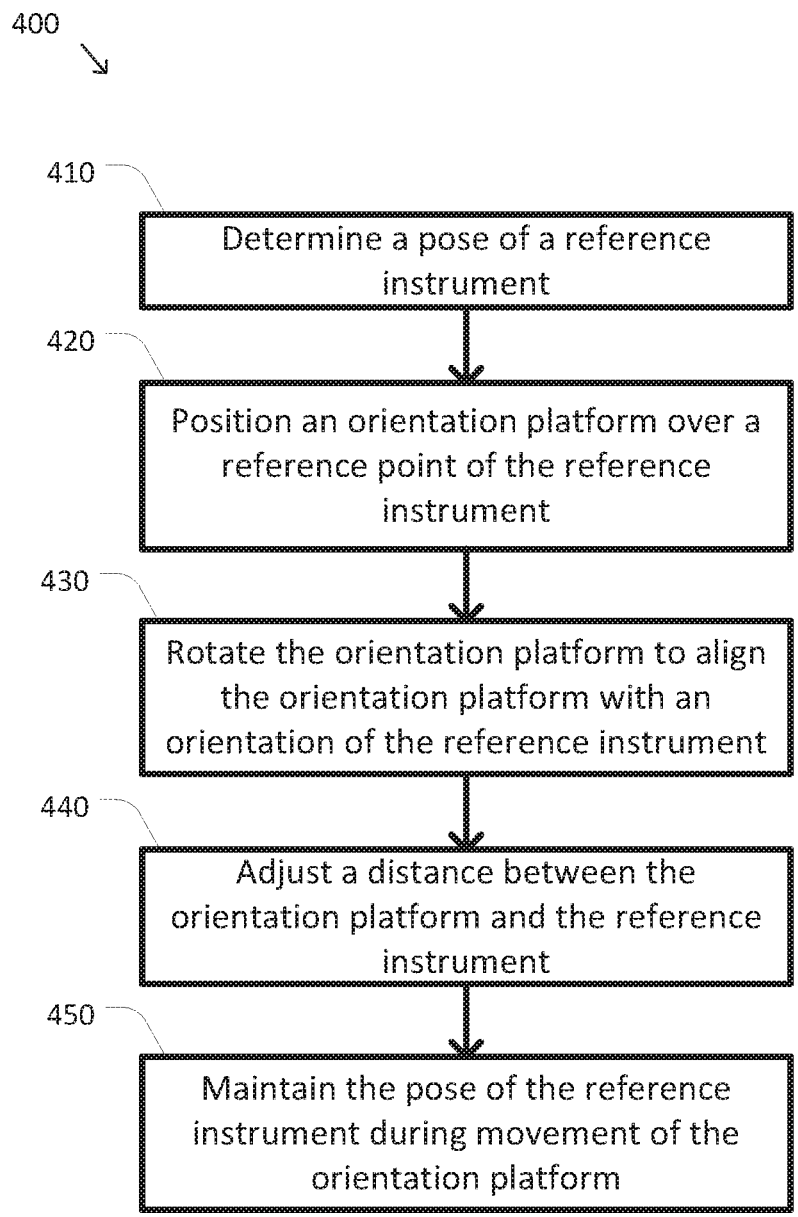
FIG. 4 is a simplified diagram of a method of aligning with a reference target according to some embodiments.

FIG. 4 is a simplified diagram of a method 400 of aligning with a reference target according to some embodiments. One or more of the processes 410-450 of method 400 may be implemented, at least in part, in the form of executable code stored on non-transient, tangible, machine readable media that when run by one or more processors (e.g., the processor 140 in control unit 130) may cause the one or more processors to perform one or more of the processes 410-450. In some embodiments, method 400 may be performed by an application, such as motion control application 160. In some embodiments, method 400 may be used to adjust positions and/or orientations of various joints and links in the set-up structure, set-up joints, and/or manipulator joints of a computer-assisted device while maintaining the pose (position and orientation) of a reference instrument.

At a process 410, a pose of a reference instrument is determined. The reference target for the alignment or targeting operation of method 400 is based on the pose (position and orientation) of a reference instrument. The reference instrument is typically located at the distal end of an articulated arm of a computer-assisted device. In some examples, one or more sensors associated with joints and links of the articulated arm and the computer-assisted device and one or more kinematic models of the articulated arm and the computer-assisted device may be used to determine the position and orientation of the reference instrument. In some examples, the pose of the reference instrument may be determined based on a reference point on the reference instrument and a reference orientation of the reference instrument. In some examples, the reference instrument may have been previously posed, either manually or with computer assistance, by an operator of the computer-assisted device. In some examples, the operator may initiate determination of the pose of the reference instrument using one or more control inputs. In some examples, the articulated arm may be the articulated arm 320 and reference instrument may be the instrument 262, with the pose of the reference instrument being determined by the remote center 270 and the orientation axis 360.

At a process 420, an orientation platform is positioned over a reference point of the reference instrument. To better position the orientation platform over a desired workspace for the computer-assisted device, one or more joints of the computer-assisted device that are proximal to the orientation platform are commanded to move the orientation platform of the computer-assisted device so that it is positioned over the reference point determined during process 410. In some examples, the orientation platform may be moved so as to position a predetermined point on or near the orientation platform vertically above the reference point. In some examples, the predetermined point may be associated with a centroid and/or other central point on the orientation platform and/or an axis about which the orientation platform may be rotated. In some examples, positioning of the orientation platform may include adjusting a horizontal distance and/or an angular position of the orientation platform relative to a central column of the computer-assisted device. In some examples, one or more kinematic models and/or motion planning algorithms may be used to determine one or more movement and/or positioning commands to be sent to one or more actuators of the computer-assisted device. In some examples, when the computer-assisted device is the computer-assisted device 200, one or more of the joints in the set-up structure 220 may be commanded to position the orientation platform 227 horizontally over the remote center. In some examples, process 420 may include positioning rotational center 350 over remote center 270.

At a process 430, the orientation platform is rotated to align the orientation platform with an orientation of the reference instrument. To provide for improved range of motion in the reference instrument, the orientation platform may be rotated to align the orientation platform with the orientation of the reference instrument determined during process 410. In some examples, the orientation platform may be rotated to align a predetermined orientation vector of the orientation platform with the orientation of the reference instrument. In some examples, the orientation platform may be rotated about its axis of rotation so that a first set-up joint in the articulated arm to which the reference instrument is attached is at or near its rotational range of motion. In some examples, the orientation platform may be rotated using or more rotational joints, such as a wrist joint, located proximal to the orientation platform. In some examples, one or more kinematic models and/or motion planning algorithms may be used to determine one or more movement and/or positioning commands to be sent to one or more actuators of the computer-assisted device. In some examples, process 430 may be performed concurrently with process 420. In some examples, process 430 may be omitted when the orientation of the reference instrument does not include a horizontal component. In some examples, when the computer-assisted device is the computer-assisted device 200, the orientation platform 227 may be rotated about axis 236 and rotational center 350 using wrist joint 226 in order to align the front face orientation vector 370 with a horizontal component of the orientation axis 360.

At an optional process 440, a distance between the orientation platform and the reference instrument may be adjusted. In some examples, the distance between the predetermined point on the orientation platform and the reference point of the reference instrument may be adjusted. In some examples, the distance of the orientation platform may be adjusted to place joints in the articulated arm near centers of their respective ranges of motion, to reduce the likelihood of collisions between the articulated arm and/or the reference instrument with the set-up structure of the computer-assisted device, to help maintain a sterile field around the reference instrument, and/or to maintain a predetermined distance determined by an operator. In some examples, the distance may be the vertical distance between the reference point determined during process 410 and the predetermined point aligned during process 420. In some examples, the distance between the orientation platform and the reference instrument may be adjusted using one or more joints located proximal to the orientation platform. In some examples, one or more kinematic models and/or motion planning algorithms may be used to determine one or more movement and/or positioning commands to be sent to one or more actuators of the computer-assisted device. In some examples, process 440 may be performed concurrently with processes 420 and/or 430.

At a process 450, the pose of the reference instrument is maintained during movement of the orientation platform. While the orientation platform is being moved during processes 420, 430, and/or 440, the pose of the reference instrument relative to a workspace for the computer-assisted device is maintained. The pose is maintained even though the position and/or orientation of the reference instrument relative to the orientation platform may be changing. This may be accomplished by adjusting one or more joints of the articulated arm distal to the orientation platform in response to the movements of the one or more joints proximal to the orientation platform that are being commanded during processes 420, 430, and/or 440.

As discussed above and further emphasized here, FIG. 4 is merely an example which should not unduly limit the scope of the claims. One of ordinary skill in the art would recognize many variations, alternatives, and modifications. According to some embodiments, one or more of the processes 420-450 may be performed concurrently. According to some embodiments, additional conditions may result in premature termination of method 400 such as by returning control of the computer-assisted device to an operator and/or by suspension of operation of the computer-assisted device. In some examples, the additional conditions may include inability to complete the desired movement, manual intervention and/or override from an operator using one or more controls on an operator workstation and/or the articulated arms, detection of operator disengagement with the operator workstation using one or more safety interlocks, position tracking errors in the computer-assisted device, system faults, and/or the like. In some examples, the desired movement may not be possible due to the detection of imminent collisions among the links and/or joints of the computer-assisted device, range of motion limits in one or more of the joints of the computer-assisted device, inability to position and/or orient the orientation platform while maintaining the pose of the reference instrument during process 450, and/or the like. In some examples, premature termination of method 400 may result in an error notification being sent to the operator. In some examples, the error notification may include a text message, an audio indicator, a spoken phrase, and/or the like.

Figure 5:
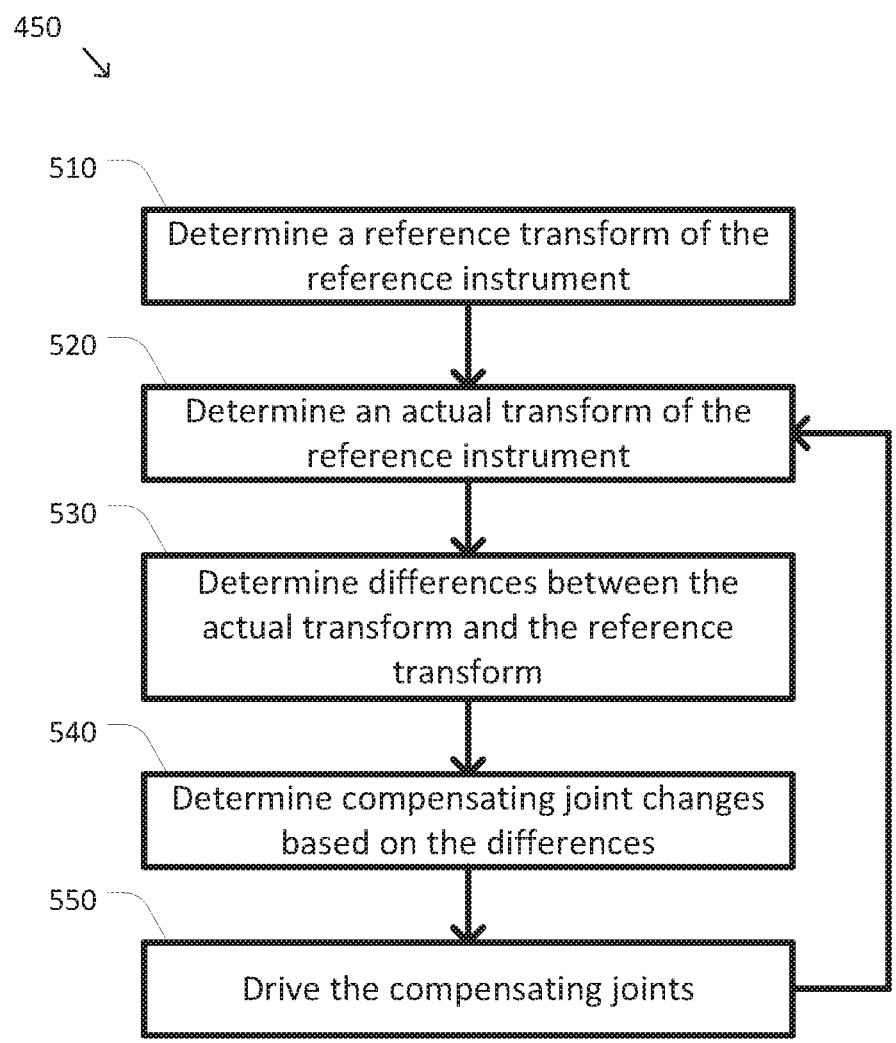
FIG. 5 is a simplified diagram of a process of maintaining a pose of a reference instrument during movement of an orientation platform according to some embodiments.

FIG. 5 is a simplified diagram of the process 450 of maintaining the pose of the reference instrument during movement of the orientation platform according to some embodiments. As the orientation platform is being positioned and oriented during processes 420, 430, and/or 440, the movements of the orientation platform affect each of the links and joints of the articulated arm distal to the orientation platform, including the reference instrument. As these movements introduce changes in the pose of the reference instrument, processes 510-550 compensate for those changes so that the pose of the reference instrument is maintained.

At a process 510, a reference transform of the reference instrument is determined. Prior to the initiation of movement during processes 420, 430, and/or 440, one or more kinematic models of the computer-assisted device are used to determine a reference transform for the reference instrument. In some examples, the one or more kinematic models may include one or more kinematic models for the set-up structure proximal to the orientation platform, the set-up joints distal to the orientation platform, and/or the manipulator to which the reference instrument is attached. In some examples, the reference transform may model the pose of the reference instrument in a world coordinate system for the computer-assisted device and/or the workspace of which the reference instrument is a part.

At a process 520, an actual transform of the reference instrument is determined. As the joints proximal to the orientation platform are commanded during processes 420, 430, and/or 440, the pose of the reference instrument begins to change because the reference instrument is distal to the orientation platform. The commanded changes in joint positions and/or angles in the joints proximal to the orientation platform are monitored and the one or more kinematic models are again applied to determine the actual transform of the reference instrument. The actual transform represents how the movements of processes 420, 430, and/or 440 are tending to move the reference instrument away from its desired pose.

At a process 530, differences between the actual transform and the reference transform are determined. The differences between the actual transform and the reference transform represent errors that would be introduced into the pose of the reference instrument unless they are compensated for by changes in joint positions and/or angles in the joints distal to the orientation platform. In some examples, the differences may be determined by subtracting corresponding matrix and/or vector representations of the action and reference transforms.

At a process 540, compensating joint changes are determined based on the differences. Using the differences between the actual transform and the reference transform determined during process 530, one or more compensating joint changes is determined. Because the compensating joints are located distal to the orientation platform, the differences between the actual transform and the reference transform is mapped from the world coordinate system of the actual and reference transforms to a local coordinate system based on the compensating joints. In effect, this transforms the errors in the absolute pose of the reference instrument from the world coordinate system to relative errors in the pose between the reference instrument and the most proximal of the compensating joints. In some examples, one or more kinematic models may be used to transform the differences to the local coordinate system. In some examples, the compensating joints may include one or more of the manipulator joints. In some examples, compensating joints may further include one or more of the set-up joints between the orientation platform and the manipulator. Once the relative errors in the pose are determined, they may be used to determine the compensating joint changes. In some examples, an inverse Jacobian may be used to map the relative errors to the compensating joint changes. In some examples, the compensating joint changes may include joint velocities for the compensating joints.

At a process 550, the compensating joints are driven. One or more commands are sent to the one or more actuators in the compensating joints based on the compensating joint changes determined during process 540. The commands sent to the compensating joints correct for the errors in the pose of the reference instrument introduced by the movements in the joints proximal to the orientation platform so that the pose of the reference instrument in the world coordinate system is maintained with minimal error. As long as processes 420, 430, and/or 440 continue to makes changes to the position and/or orientation of the orientation platform, processes 520-550 are repeated to compensate for any errors introduced into the pose of the reference instrument.

As discussed above and further emphasized here, FIG. 5 is merely an example which should not unduly limit the scope of the claims. One of ordinary skill in the art would recognize many variations, alternatives, and modifications. According to some embodiments, the compensating joints may include a subset of the joints in the set-up joints and/or the manipulator. In some examples, the compensating joints may include just the roll, pitch, and yaw joints of the manipulator. In some examples, other joints in the manipulator and/or the set-up joints may be locked to prevent relative movement during processes 510-550. In some examples, one or more non-actuated joints of the set-up joints and/or the manipulator distal to the orientation platform may be unlocked during processes 510-550 so that errors in the pose of the reference instrument may be at least partially reduced by changes in the unlocked joints. In some examples, the changes in the unlocked joints may reduce the amount that the compensating joints are to be driven. In some examples, the pose of the reference instrument may be at least partially maintained using resistance from a patient port and/or by an operator of the computer-assisted device.

Some examples of control units, such as control unit 130 may include non-transient, tangible, machine readable media that include executable code that when run by one or more processors (e.g., processor 140) may cause the one or more processors to perform the processes of method 400. Some common forms of machine readable media that may include the processes of method 400 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A computer-assisted medical device comprising:
    a first link;
    one or more first joints coupled proximally to the first link;
    an articulated arm comprising one or more second joints coupled distally to the first link, the articulated arm configured to couple to an instrument; and
    a control unit, wherein the control unit is configured to:
        position or orient the first link, using the one or more first joints, based on at least one reference of the instrument selected from a group consisting of: a reference point associated with the instrument and a reference orientation of the instrument; and
        maintain, while positioning or orienting the first link and by using the one or more second joints, a position or an orientation of the instrument relative to a workspace in accordance with the at least one reference of the instrument.

2. The computer-assisted medical device of claim 1, wherein the control unit is further configured to:
    both position and orient the first link, using the one or more first joints, based on both the reference point associated with the instrument and the reference orientation of the instrument; and
    maintain, while positioning and orienting the first link, both the position and the orientation of the instrument relative to the workspace in accordance with the reference point and the reference orientation.

3. The computer-assisted medical device of claim 1, wherein the first link is an orientation platform, wherein the reference point is a remote center of the instrument, and wherein the instrument comprises an imaging device.

4. The computer-assisted medical device of claim 1, wherein the control unit is further configured to:
    unlock, while positioning or orienting the first link, at least one of the one or more second joints.

5. The computer-assisted medical device of claim 4, wherein the control unit is further configured to:
    lock, while positioning or orienting the first link, at least one other joint of the one or more second joints.

6. The computer-assisted medical device of claim 1, further comprising:
    an additional articulated arm coupled distally to the first link, the additional articulated arm comprising a third joint,
    wherein the control unit is further configured to: place, while positioning or orienting the first link, the third joint in a float state.

7. The computer-assisted medical device of claim 6, wherein the control unit is configured to place the third joint in the float state by: at least partially releasing a brake associated with the third joint.

8. The computer-assisted medical device of claim 6, wherein the control unit is further configured to:
    command, when the third joint is in the float state, the third joint to an actual position or an actual velocity of the third joint.

9. The computer-assisted medical device of claim 6, wherein the control unit is further configured to:
    command, when the third joint is in the float state, the third joint to a position between an actual position and a commanded position of the third joint, or to a velocity lower than an actual velocity of the third joint.

10. The computer-assisted medical device of claim 6, wherein the control unit is configured to place the third joint in the float state while positioning or orienting the first link by: introducing a resisting force or torque on the third joint.

11. The computer-assisted medical device of claim 1, wherein the control unit is further configured to:
    adjust a distance between the first link and the reference point to maintain a sterile field or to maintain a working height of the first link above the reference point.

12. The computer-assisted medical device of claim 1, wherein the reference point is associated with a point on patient anatomy through which the instrument is inserted.

13. The computer-assisted medical device of claim 1, wherein the control unit is configured to position the first link using the one or more first joints based on the reference point associated with the instrument by:
    positioning a centroid of the first link vertically above the reference point; or
    positioning a rotational center of the first link vertically above the reference point.

14. A method of controlling motion in a computer-assisted medical device, the method comprising:
    positioning or orienting, by one or more processors, a first link of the computer-assisted medical device, using one or more first joints proximal to the first link, based on at least one reference of an instrument coupled to an articulated arm of the computer-assisted medical device, the articulated arm comprising one or more second joints coupled distally to the first link, the at least one reference of the instrument being selected from a group consisting of: a reference point associated with the instrument and a reference orientation of the instrument; and
    maintaining, by the one or more processors and while positioning or orienting the first link by using the one or more second joints, a position or an orientation of the instrument relative to a workspace in accordance with the at least one reference of the instrument.

15. The method of claim 14, further comprising:
both positioning and orienting the first link, using the one or more first joints, based on both the reference point associated with the instrument and the reference orientation of the instrument; and
maintaining, while positioning and orienting the first link, both the position and the orientation of the instrument relative to the workspace in accordance with the reference point and the reference orientation.

16. The method of claim 14, wherein the first link is an orientation platform, wherein the reference point is a remote center of the instrument, and wherein the instrument comprises an imaging device.

17. The method of claim 14, further comprising:
unlocking, while positioning or orienting the first link, at least one of the one or more second joints.

18. The method of claim 17, further comprising:
locking, while positioning or orienting the first link, at least one other joint of the one or more second joints.

19. The method of claim 14, further comprising:
placing, while positioning or orienting the first link, a third joint of an additional articulated arm distal to the first link in a float state.

20. The method of claim 14, further comprising:
adjusting a distance between the first link and the reference point to maintain a sterile field or maintain a working height of the first link above the reference point.

21. The method of claim 14, wherein the reference point is associated with a point on patient anatomy through which the instrument is inserted.

* * * * *

UNITED STATES PATENT AND TRADEMARK OFFICE
CERTIFICATE OF CORRECTION

PATENT NO. : 10,610,316 B2
APPLICATION NO. : 16/052555
DATED : April 7, 2020
INVENTOR(S) : Nitish Swarup et al.

Page 1 of 1

It is certified that error appears in the above-identified patent and that said Letters Patent is hereby corrected as shown below:

On the Title Page

(63) Related U.S. Application Data:
Please delete "Continuation of application No. 15/126,983, filed as application No. PCT/US2015/021097 on Mar. 17, 2015, now Pat. No. 10,064,689." and insert --Continuation of application No. 15/126,983, filed on Sep. 16, 2016, now Pat. No. 10,064,689, which is a 371 of application No. PCT/US2015/021097, filed on Mar. 17, 2015.--.

Signed and Sealed this
Twenty-sixth Day of May, 2020

Andrei Iancu
*Director of the United States Patent and Trademark Office*